(12) United States Patent
Bertini et al.

(10) Patent No.: US 11,311,397 B2
(45) Date of Patent: Apr. 26, 2022

(54) BRANCH STENT GRAFT AND DELIVERY METHOD FOR ENDOVASCULAR TREATMENT OF THE ILIAC ARTERY ANEURYSMS

(71) Applicant: Medtronic Vascular, Inc., Santa Rosa, CA (US)

(72) Inventors: Timothy Bertini, Santa Rosa, CA (US); Adam Shipley, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 69 days.

(21) Appl. No.: 16/661,343

(22) Filed: Oct. 23, 2019

(65) Prior Publication Data

US 2021/0121309 A1    Apr. 29, 2021

(51) Int. Cl.
| | | |
|---|---|---|
| *A61F 2/954* | (2013.01) | |
| *A61F 2/07* | (2013.01) | |
| *A61F 2/966* | (2013.01) | |
| *A61F 2/95* | (2013.01) | |
| *A61F 2/06* | (2013.01) | |

(52) U.S. Cl.
CPC ............... *A61F 2/954* (2013.01); *A61F 2/07* (2013.01); *A61F 2/966* (2013.01); *A61F 2/9517* (2020.05); *A61F 2002/067* (2013.01); *A61F 2002/9665* (2013.01)

(58) Field of Classification Search
CPC .. A61F 2/954; A61F 2/966; A61F 2/07; A61F 2/9517; A61F 2002/9665; A61F 2002/067; A61F 2/95; A61F 2/958; A61F 2/962; A61F 2002/065; A61F 2/9665; A61F 2250/0006
See application file for complete search history.

(56) References Cited

U.S. PATENT DOCUMENTS

| | | |
|---|---|---|
| 5,653,743 A | 8/1997 | Martin |
| 5,928,248 A | 7/1999 | Acker |
| 7,846,194 B2 | 12/2010 | Hartley et al. |
| 8,021,412 B2 | 9/2011 | Hartley et al. |
| 8,292,941 B2 | 10/2012 | Muzslay |
| 8,945,200 B1 | 2/2015 | Eblacas et al. |
| 9,066,793 B2 | 6/2015 | Hung et al. |
| 9,408,689 B2 | 8/2016 | Buddery et al. |

(Continued)

FOREIGN PATENT DOCUMENTS

WO    02030329 A2    4/2002

OTHER PUBLICATIONS

PCT/US2020/042984, The International Search Report, dated Sep. 24, 2020, 11pages.

*Primary Examiner* — Diane D Yabut

(74) *Attorney, Agent, or Firm* — Innovation Counsel LLP

(57) ABSTRACT

An iliac branch device has an external iliac body, a common iliac branch, and an internal iliac branch. A diameter of the proximal opening of the common iliac branch is greater than a diameter of a distal opening of the external iliac body. The iliac branch device is configured to be deployed without going up and over the aortic bifurcation and without using some form of supra-aortic antegrade access such as through brachial or axillary artery access. This simplifies the procedure and reduces procedure time thus maximizing the success rate of the procedure and allows the procedure to be performed on a broad patient population.

23 Claims, 12 Drawing Sheets

(56) References Cited

U.S. PATENT DOCUMENTS

| | | |
|---|---|---|
| 9,545,324 B2 | 1/2017 | Roeder |
| 9,603,734 B2 | 3/2017 | Hartley et al. |
| 9,642,732 B2 | 5/2017 | Barrand |
| 9,782,284 B2 | 10/2017 | Hartley et al. |
| 9,788,982 B2 | 10/2017 | Hartley et al. |
| 9,808,365 B2 | 11/2017 | Hartley et al. |
| 10,034,785 B1 | 7/2018 | Schonholz et al. |
| 10,105,245 B2 | 10/2018 | Ondersma et al. |
| 10,130,501 B2 | 11/2018 | Roeder et al. |
| 10,166,095 B2 | 1/2019 | Hartley |
| 10,201,414 B2 | 2/2019 | Hartley et al. |
| 2001/0014823 A1 | 8/2001 | Ressemann et al. |
| 2006/0247761 A1 | 11/2006 | Greenberg et al. |
| 2009/0216308 A1* | 8/2009 | Hartley .................. A61F 2/07 623/1.11 |
| 2011/0066221 A1* | 3/2011 | White .................... A61F 2/07 623/1.11 |
| 2012/0150273 A1* | 6/2012 | Centola .................. A61F 2/07 623/1.12 |
| 2013/0041456 A1* | 2/2013 | Greenberg .............. A61F 2/07 623/1.35 |
| 2013/0166015 A1 | 6/2013 | Roeder |
| 2014/0277330 A1* | 9/2014 | Roeder ................ A61F 2/966 623/1.11 |
| 2015/0018932 A1* | 1/2015 | Buddery ................ A61F 2/07 623/1.13 |
| 2015/0051692 A1* | 2/2015 | Teague .................. A61F 2/856 623/1.13 |
| 2015/0057737 A1 | 2/2015 | Ondersma et al. |
| 2016/0262919 A1 | 9/2016 | Ondersma et al. |
| 2017/0128190 A1 | 5/2017 | Batiste et al. |
| 2017/0296324 A1* | 10/2017 | Argentine ............. A61F 2/844 |
| 2018/0116838 A1 | 5/2018 | Shrum et al. |

\* cited by examiner

BRANCH STENT GRAFT AND DELIVERY METHOD FOR ENDOVASCULAR TREATMENT OF THE ILIAC ARTERY ANEURYSMS

FIELD

The present technology is generally related to an intravascular device and method. More particularly, the present application relates to a device for treatment of intra-vascular diseases.

BACKGROUND

Iliac artery aneurysms in close proximity to the iliac bifurcation present an unmet clinical need for vascular surgeons versed in endovascular repair. One treatment option includes open surgery, which is highly invasive with associated long recovery and hospital stay times.

Another treatment option includes sacrificing the internal iliac artery by covering the internal iliac artery with a stent graft. Unfortunately, covering the internal iliac artery leads to poor quality of life from complications related to groin ischemia.

Yet another treatment option involves sealing a stent graft in the diseased (aneurysmal) common iliac artery. However, this option is associated with high rates of degeneration leading to future complications and reinterventions.

Challenges in the above options often lead the vascular surgeon to used limited commercially available iliac branch stent graft systems. The available iliac branch stent graft systems require high skill level, multiple accessory devices, and multiple surgical access points.

SUMMARY

The techniques of this disclosure generally relate to an iliac branch device having an external iliac body, a common iliac branch, and an internal iliac branch. A diameter of the proximal opening of the common iliac branch is greater than a diameter of a distal opening of the external iliac body. The iliac branch device is configured to be deployed without going up and over the aortic bifurcation and without using some form of supra-aortic antegrade access such as through brachial or axillary artery access. This simplifies the procedure and reduces procedure time thus maximizing the success rate of the procedure and allows the procedure to be performed on a broad patient population.

In one aspect, the present disclosure provides an assembly comprising an inner member and an iliac branch device having the inner member therein. The iliac branch device includes an external iliac body configured to be located within an external iliac artery, a common iliac branch configured to be located with a common iliac artery, and an internal iliac branch configured to perfuse an internal iliac artery.

In another aspect, the present disclosure provides a method comprising loading an iliac branch device within a delivery system having a handle. The iliac branch device includes an external iliac body, a common iliac branch, and an internal iliac branch. The external iliac body is proximal to both the common iliac branch and the internal iliac branch relative to the handle.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
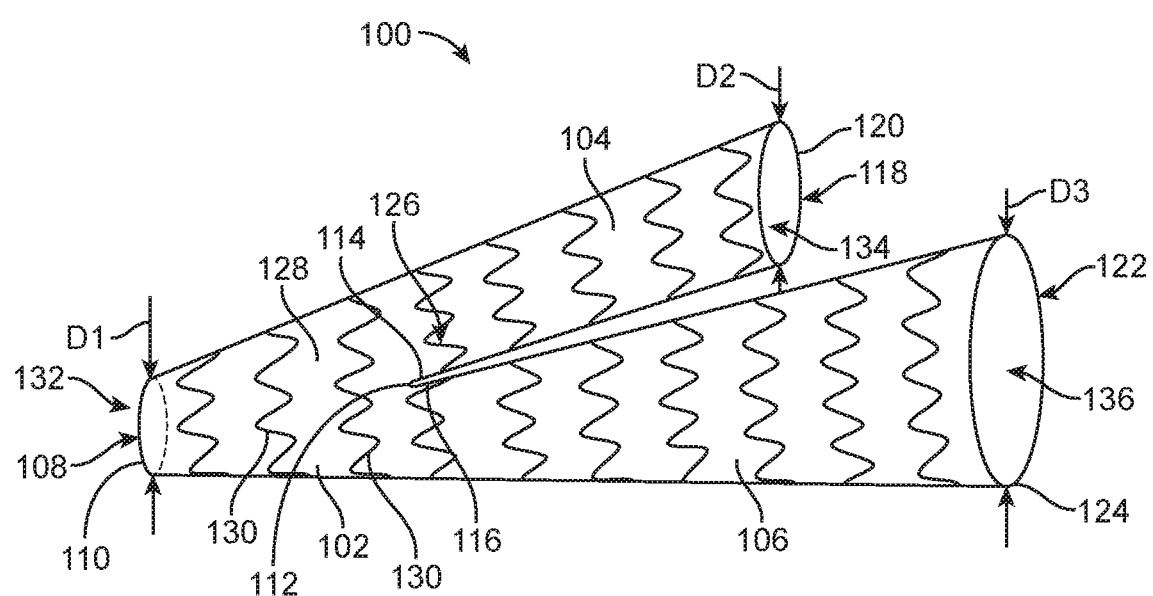
FIG. 1 is a perspective view of an iliac branch device in accordance with one embodiment.

FIG. 1 is a perspective view of an iliac branch device 100 in accordance with one embodiment. Iliac branch device 100 includes an external iliac body 102, internal iliac branch 104, and a common iliac branch 106. External iliac body 102, internal iliac branch 104, and common iliac branch 106 are sometimes called an external iliac body 102, a first bifurcated leg 104, and a second bifurcated leg 106, respectively.

In accordance with this embodiment, external iliac body 102 includes distal opening 108 at a distal end 110 of external iliac body 102. A proximal end 112 of external iliac body 102 is coupled to a proximal end 114 of internal iliac branch 104 and a distal end 116 of common iliac branch 106.

Internal iliac branch 104 includes an internal iliac distal opening 118 at a distal end 120 of internal iliac branch 104. Common iliac branch 106 includes a common iliac proximal opening 122 at a proximal end 124 of common iliac branch 106.

As used herein, the proximal end of a prosthesis such as iliac branch device 100 is the end closest to the heart via the path of blood flow whereas the distal end is the end furthest away from the heart during deployment. As discussed below, blood flow enters into proximal opening 122 of common iliac branch 106 and exits distal openings 108, 118 of external iliac body 102 and internal iliac branch 104 respectively. Generally, there is retrograde blood flow through internal iliac branch 104. Accordingly, proximal end 112 of external iliac body 102 is coupled to proximal end 114 of internal iliac branch 104 and distal end 116 of common iliac branch 106 at a transition region 126.

In contrast and of note, the distal end of the delivery system is usually identified to the end that is farthest from the operator/handle while the proximal end of the delivery system is the end nearest the operator/handle. For purposes of clarity of discussion, as used herein, the distal end of the delivery system is the end that is farthest from the operator (the end furthest from the handle). However, those of skill in the art will understand that depending upon the access location, iliac branch device 100 and/or the delivery system descriptions may be different in actual usage.

Iliac branch device 100 includes graft material 128 and one or more circumferential stents 130 coupled to graft material 128. Graft material 128 may be any suitable graft material, for example and not limited to, woven polyester, DACRON® material, expanded polytetrafluoroethylene, polyurethane, silicone, electro spun materials, or other suitable materials.

Circumferential stents 130 may be coupled to graft material 128 using stitching or other means. In the embodiment shown in FIG. 1, circumferential stents 130 are coupled to an outside surface of graft material 128. However, circumferential stents 130 may alternatively be coupled to an inside surface of graft material 128.

Although shown with a particular number of circumferential stents 130, in light of this disclosure, those of skill in the art will understand that iliac branch device 100 may include a greater or smaller number of stents 130, e.g., depending upon the desired length of external iliac body 102, internal iliac branch 104, and common iliac branch 106 and/or the intended application thereof.

Circumferential stents 130 may be any stent material or configuration. As shown, circumferential stents 130, e.g., self-expanding members, are preferably made from a shape memory material, such as nickel-titanium alloy (nitinol), and are formed into a zig-zag configuration. The configuration of circumferential stents 130 is merely exemplary, and circumferential stents 130 may have any suitable configuration, including but not limiting to a continuous or non-continuous helical configuration. In another embodiment, circumferential stents 130 are balloon expandable stents. In one embodiment, bare stents and/or delivery system interfaces which increase control over delivery are included. Further, in one embodiment, there are radiopaque markers that assist in orientating iliac branch device 100.

A lumen 132 is defined by external iliac body 102. Lumen 132 extends between distal opening 108 and proximal end 112 of external iliac body 102. External iliac body 102 increases in diameter from distal opening 108 to proximal end 112. However, in other embodiments, external iliac body 102 is uniform in diameter or decreases in diameter from distal opening 108 to proximal end 112.

Further, a lumen 134 is defined by internal iliac branch 104. Lumen 134 extends between proximal end 114 and distal opening 118 of internal iliac branch 104. Internal iliac branch 104 is cylindrical having a substantially uniform diameter in this embodiment. However, in other embodiments, internal iliac branch 104 varies in diameter.

Further, a lumen 136 is defined by common iliac branch 106. Lumen 136 extends between proximal opening 122 and distal end 116 of common iliac branch 106. Common iliac branch 106 decreases in diameter from proximal opening 122 to distal end 116. However, in other embodiments, common iliac branch 106 is uniform in diameter or increases in diameter from proximal opening 122 to distal end 116.

Generally, external iliac body 102 is bifurcated at proximal end 112 (transition region 126) into internal iliac branch 104 and common iliac branch 106. More particularly, lumen 132 of external iliac body 102 is bifurcated into lumen 134 of internal iliac branch 104 and lumen 136 of common iliac branch 106.

In accordance with this embodiment, openings 108, 118, and 122 of external iliac body 102, internal iliac branch 104, and common iliac branch 106 have diameters D1, D2, and D3, respectively, in their relaxed and expanded configuration. Illustratively, diameter D3 is in the range of 12 to 28 millimeters (mm), diameter D2 is less than 12 mm, and diameter D1 is in the range of 8 to 14 mm.

In one embodiment, diameter D3 of opening 122 of common iliac branch 106 is greater than either of diameters D1 and D2 of opening 108 of external iliac body 102 and opening 118 of internal iliac branch 104, respectively. However, in other embodiments, diameter D1 is greater than or equal to diameter D3, e.g., diameter D3 is 12 mm and diameter D1 is up to 14 mm.

Figure 2:
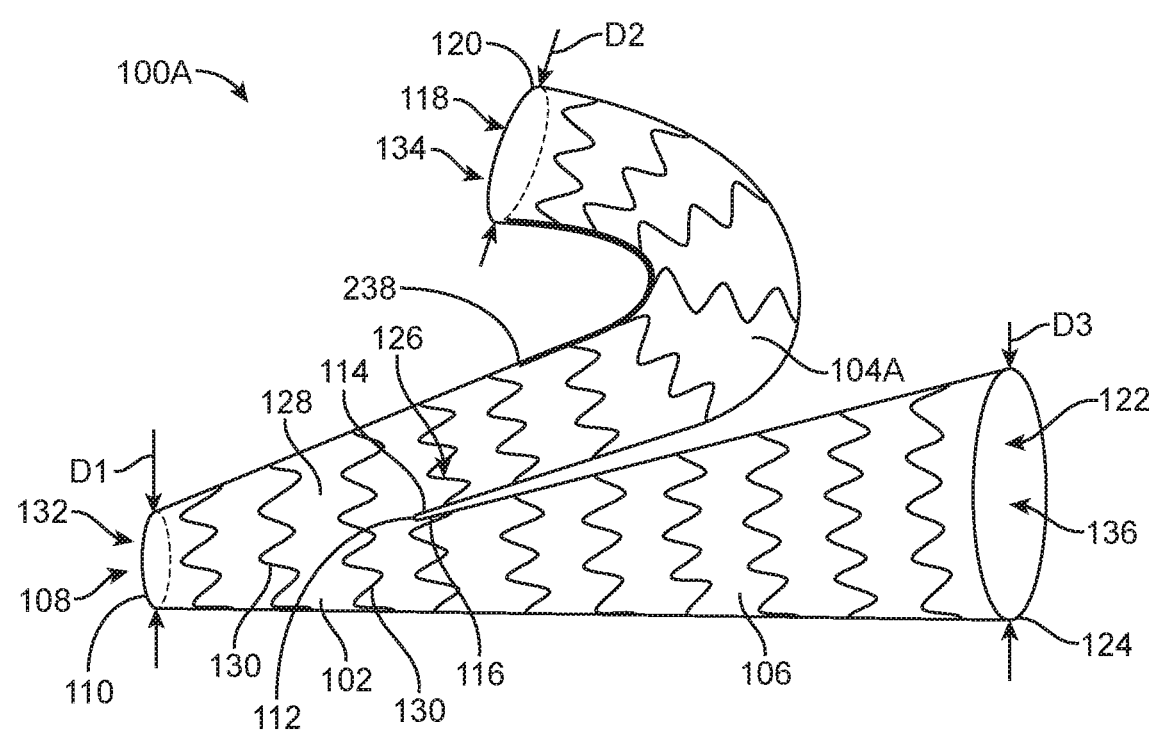
FIG. 2 is a perspective view of an iliac branch device in accordance with another embodiment.

FIG. 2 is a perspective view of an iliac branch device 100A in accordance with another embodiment. Iliac branch device 100A of FIG. 2 is similar to iliac branch device 100 of FIG. 1 and only the significant differences are discussed below. More particularly, iliac branch device 100A includes external iliac body 102 and common iliac branch 106 which are similar or identical to external iliac body 102 and common iliac branch 106 of iliac branch device 100 and so are not discussed further.

Referring now to FIG. 2, an internal iliac branch 104A is curved, sometimes called having a hook shape, a "J" shape, or a "candy cane" shape. More particular, internal iliac branch 104A curves away from common iliac branch 106 such that distal opening 118 points away from common iliac branch 106. The curved shape of internal iliac branch 104A facilitates cannulation of the internal iliac artery as discussed further below.

In one embodiment, internal iliac branch 104A includes a curving member 238 that curves internal iliac branch 104A. Curving member 238 includes a curved wire, stitching, or other feature that curves internal iliac branch 104A in various embodiments. A pre-shaped, curved wire could be constructed from a superelastic or traditional alloy and be attached to the inner curve of the flexible internal iliac branch 104A to force curvature. The attachment could be to the inside or outside of internal iliac branch 104A by way of suture material. Alternatively, a seamed channel could be created in the graft material of internal iliac branch 104A with the wire floating freely inside. A second (or multiple) wires(s) could further act to form this shape. Alternatively, a stitching pattern could establish a morphology of the graft material of internal iliac branch 104A that when pressurized would assume the hook shape, thus eliminating the need for a wire member.

Figure 3:
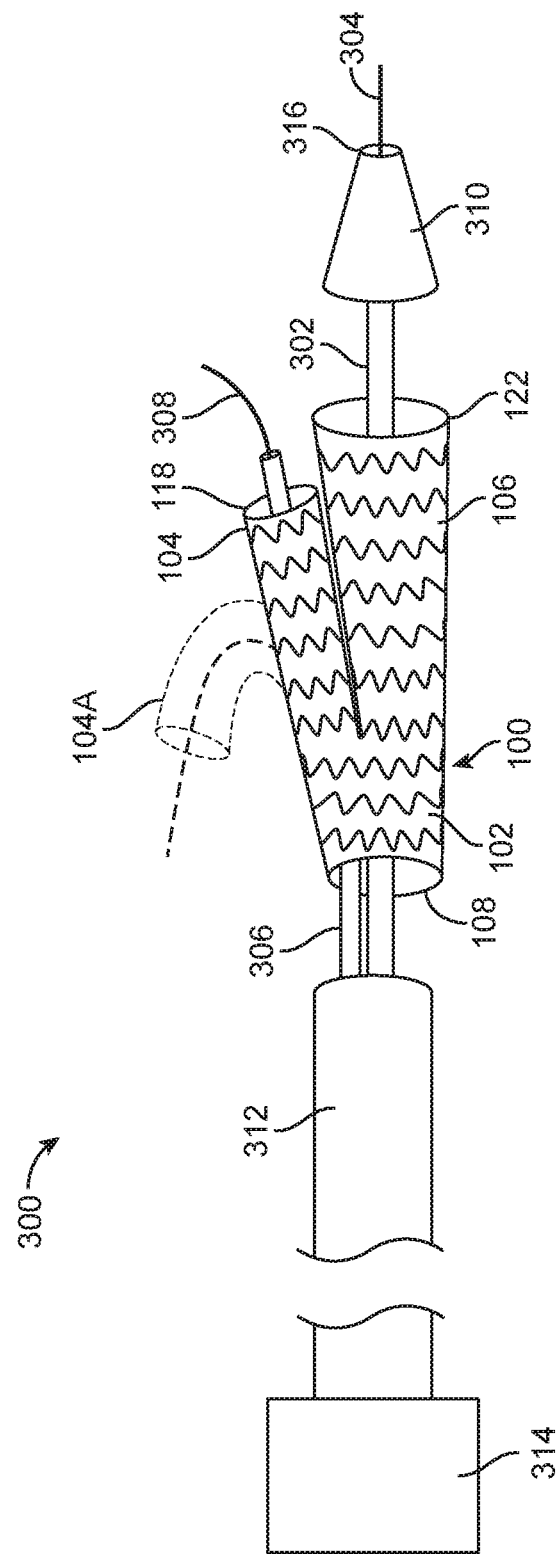
FIG. 3 is a perspective view of a delivery system including the iliac branch device of FIG. 1 in accordance with one embodiment.

FIG. 3 is a perspective view of a delivery system 300 including iliac branch device 100 of FIG. 1 in accordance with one embodiment. Delivery system 300 includes a first inner member 302, a first guidewire 304, a second inner member 306, a second guidewire 308, a distal tip 310, a sheath 312, and a handle 314.

As illustrated in FIG. 3, first and second guidewires 304, 308 extend through lumens in first and second inner members 302, 306. Inner members 302, 306 and guidewires 304, 308 extend distally from handle 314 and within sheath 312.

Handle 314 has various mechanisms and ports to allow manipulation, e.g. retraction or advancement, of guidewires 304, 308, sheath 312 and/or inner members 302, 306 relative to one another.

Distal tip 310 is coupled to first inner member 302, e.g., the distal end thereof, and has a guidewire port 316 through which guidewire 304 extends. Second inner member 306 is located between first inner member 302 and sheath 312 in this embodiment.

Iliac branch device 100 is loaded within delivery system 300. More particularly, external iliac body 102 and common iliac branch 106 are loaded over first inner member 302. In other words, first inner member 302 enters distal opening 108 of external iliac body 102, extends through both external iliac body 102 and common iliac branch 106 and exits proximal opening 122 of common iliac branch 106.

Further, external iliac body 102 and internal iliac branch 104 are loaded over second inner member 306. In other words, second inner member 306 enters distal opening 108 of external iliac body 102, extends through both external iliac body 102 and internal iliac branch 104 and exits distal opening 118 of internal iliac branch 104. Second guidewire 308 is sometimes called a prewired guidewire 308 in accordance with this embodiment.

Although delivery system 300 is illustrated and discussed as including both inner members 302, 306 and guidewires 304, 308, in another embodiment, delivery system includes either inner member 302/guidewire 304 or inner member 306/guidewire 308, but not both.

Further, although a particular arrangement of loading of iliac branch device 100 within delivery system 300 is illustrated and discussed, other arrangements and delivery systems are used in other embodiments. Generally, iliac branch device 100 is loaded such that external iliac body 102 is proximal (relative to handle 314) to both internal iliac branch 104 and common iliac branch 106. Iliac branch device 100 is sometime said to be loaded backwards within the delivery system.

Two guidewires are potentially used. The primary guidewire runs through common iliac branch 106. The second guidewire runs through internal iliac branch 104. In other embodiments, a single guidewire is used. Other arrangements are possible.

FIG. 3 illustrates delivery system 300 in a deployed (or pre-loading) state where sheath 312 is withdrawn to expose iliac branch device 100 for purposes of illustrating the various features of delivery system 300. When in a delivery state, sheath 312 abuts distal tip 310 and iliac branch device 100 is constrained between sheath 312 and inner members 302, 306.

To deploy iliac branch device 100, delivery system 300 is advanced over first guidewire 304 to the desired deployment location. For example, delivery system 300 is introduced through an ipsilateral external iliac artery access point and advanced to the desired deployment location. Once at the deployment location, sheath 312 is retracted thus releasing iliac branch device 100. Once released, iliac branch device 100, e.g., stents 130, self-expands (or is balloon expanded) to be secured in the deployment location.

In one embodiment, upon retraction of sheath 312 and deployment of iliac branch device 100, iliac branch device 100 assumes a configuration similar to that illustrated in FIG. 1. In accordance with this embodiment, internal iliac branch 104 is deployed as a straight member.

In another embodiment, second inner member 306 is a resilient curved member. Second inner member 306 is constrained in a straight state by sheath 312 when in a delivery state. Upon being deployed and released from sheath 312, second inner member 306 resumes the curved state of second inner member 306. Curvature of second inner member 306 causes curvature of internal iliac branch 104 as illustrated by the dashed lines in FIG. 3.

In another embodiment, iliac branch device 100A of FIG. 2 is loaded within delivery system 300 instead of iliac branch device 100 of FIG. 1. In accordance with this embodiment, referring to FIGS. 2-3 together, internal iliac branch 104A is constrained in a straight state by sheath 312 when in a delivery state. Upon being deployed and released from sheath 312, internal iliac branch 104A resumes the curved state of internal iliac branch 104A as illustrated by the dashed lines in FIG. 3.

Figure 4:
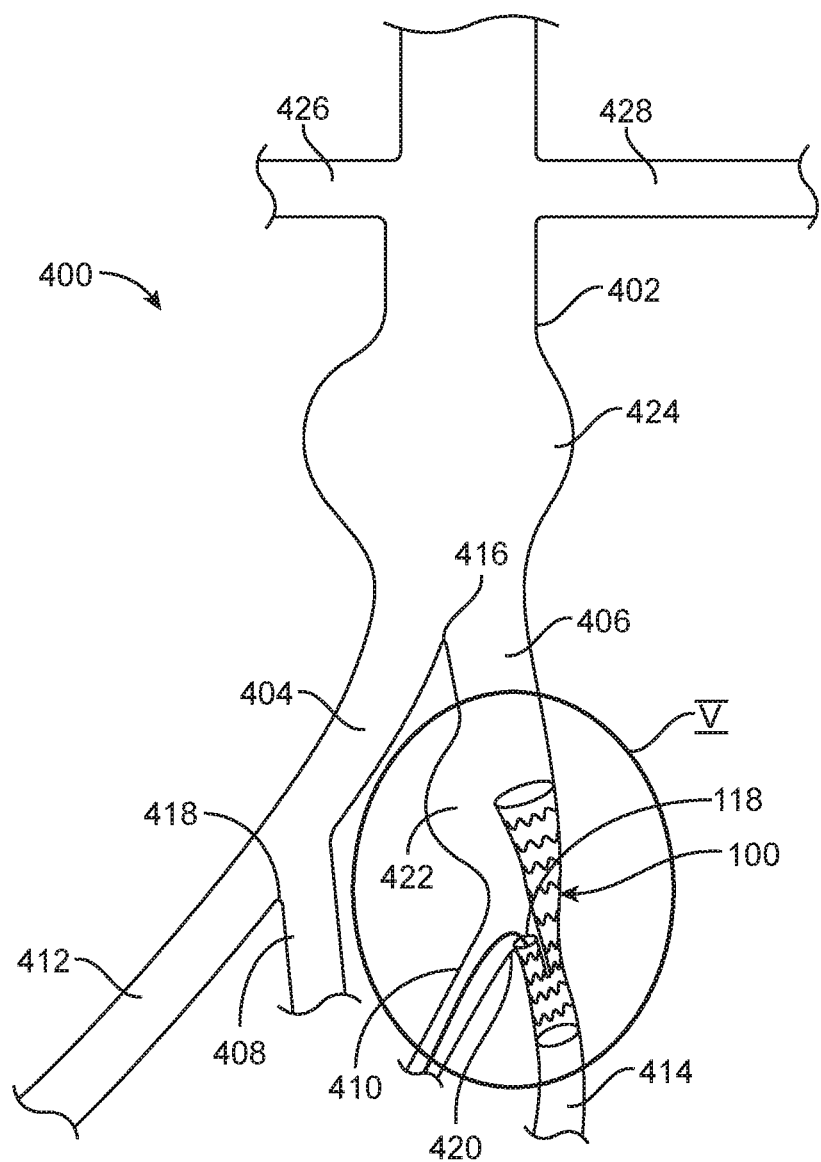
FIG. 4 is a partial cross-sectional view of a vessel assembly including the iliac branch device of FIG. 1 in accordance with one embodiment.
Figure 5:
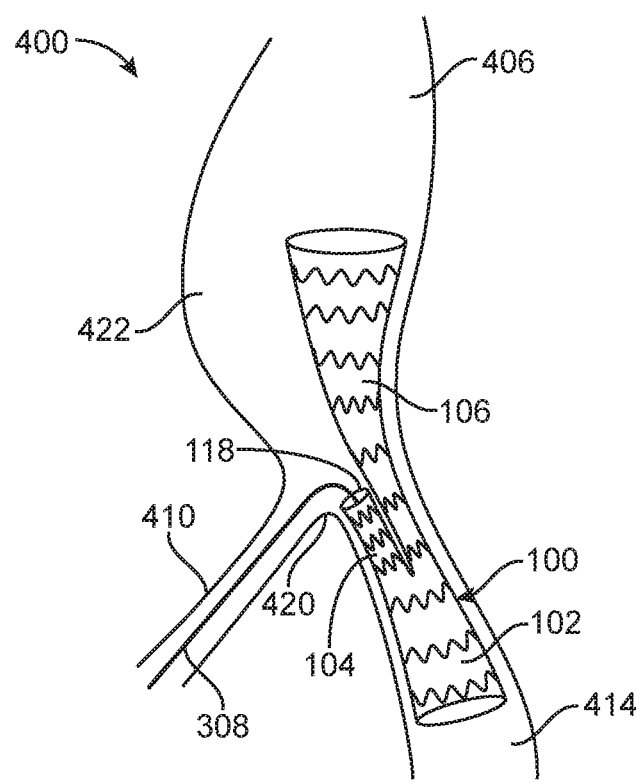
FIG. 5 is an enlarged view of the region V of the vessel assembly of FIG. 4 in accordance with one embodiment.

FIG. 4 is a partial cross-sectional view of a vessel assembly 400 including iliac branch device 100 of FIG. 1 in accordance with one embodiment. FIG. 5 is an enlarged view of the region V of vessel assembly 400 of FIG. 4 in accordance with one embodiment. Referring to FIGS. 4 and 5 together, vessel assembly 400 illustrates a series of vessels within the human body, including the aorta 402, the common iliac arteries 404, 406, internal iliac arteries 408, 410, and external iliac arteries 412, 414.

More particularly, the aorta 402 descends to an aortic bifurcation 416 from which extends common iliac arteries 404, 406. Common iliac artery 404 descends to a common iliac artery bifurcation 418 from which extends internal iliac artery 408 and external iliac artery 412 at a contralateral side. Similarly, common iliac artery 406 descends to a common iliac artery bifurcation 420 from which extends internal iliac artery 410 and external iliac artery 414 at an ipsilateral side. In accordance with this example, common iliac artery 406 includes an iliac artery aneurysm 422, i.e., a diseased section of tissue.

Referring now to FIGS. 3 and 5 together, iliac branch device 100 is deployed within common iliac artery 406 and external iliac artery 414. For example, as discussed above, delivery system 300 introduced through an ipsilateral external iliac artery access point and advanced to the desired deployment location within common iliac artery 406 and external iliac artery 414. Sheath 312 is retracted such that iliac branch device 100 is deployed with common iliac branch 106 within common iliac artery 406 and external iliac body 102 is deployed within external iliac artery 414. Distal opening 118 is adjacent to common iliac artery bifurcation 420 and generally adjacent or distal of the ostium of internal iliac artery 410. External iliac body 102 provides the distal seal within external iliac artery 414.

In accordance with this embodiment, second guidewire 308 is located within internal iliac artery 410. For example, second guidewire 308 is prewired as discussed above in reference to FIG. 3 and delivery system 300. However, in another embodiment, delivery system 300 does not include prewired guidewire 308, and guidewire 308 is advanced and manipulated to cannulate internal iliac artery 410.

Figure 6:
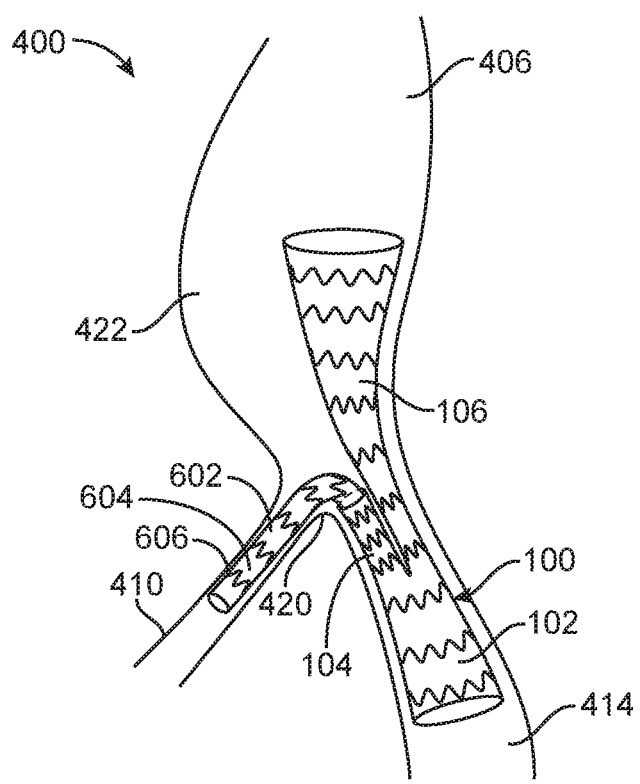
FIG. 6 is a partial cross-sectional view of the vessel assembly of FIG. 5 at a later stage during deployment of a bridging graft in accordance with one embodiment.

FIG. 6 is a partial cross-sectional view of vessel assembly 400 of FIG. 5 at a later stage during deployment of a bridging graft 602 in accordance with one embodiment. Referring now to FIGS. 5 and 6 together, bridging graft 602 is deployed within internal iliac branch 104 and internal iliac artery 410.

To deploy bridging graft 602, a delivery system including bridging graft 602 is inserted at the same access point as the access point used for iliac branch device 100, e.g., the ipsilateral external iliac artery access point. The delivery system is advanced over guidewire 308 and into internal iliac artery 410. Bridging graft 602 is then deployed from the delivery system, e.g., by withdrawing a sheath thereof. Upon deployment, bridging graft 602 self-expands (or is balloon expanded) to be located within internal iliac branch 104 and internal iliac artery 410. Guidewire 308 is removed.

Bridging graft 602 bridges blood flow from internal iliac branch 104 to internal iliac artery 410. In one embodiment, bridging graft 602 includes graft material 604 and one or more stents 606. Graft material 604 and stents 606 are the same or similar to graft material 128 and stents 130 as discussed above.

Referring now to FIGS. 1, 4, and 6 together, once deployed, blood flow enters into proximal opening 122 of common iliac branch 106. Blood flows through lumen 136 of common iliac branch 106 to transition region 126. At transition region 126, a portion of the blood flows through lumen 132 of external iliac body 102 and out distal opening 108. Another portion of the blood flows through lumen 134 of internal iliac branch 104, through bridging graft 602, and perfuses internal iliac artery 410. Blood flow through internal iliac branch 104 is retrograde (backwards) blood flow. However, there is a sufficient amount of perfusion of internal iliac artery 410 through the retrograde blood flow to avoid serious medical complication from obstruction of internal iliac artery 410.

Iliac branch device 100 and bridging graft 602 are deployed from the same ipsilateral external iliac artery access point. Of note, iliac branch device 100 and bridging graft 602 are deployed without going up and over aortic bifurcation 416 and without using some form of supra-aortic antegrade access such as through brachial or axillary artery access. This simplifies the procedure and reduces procedure time thus maximizing the success rate of the procedure and allows the procedure to be performed on a broad patient population.

Figure 7:
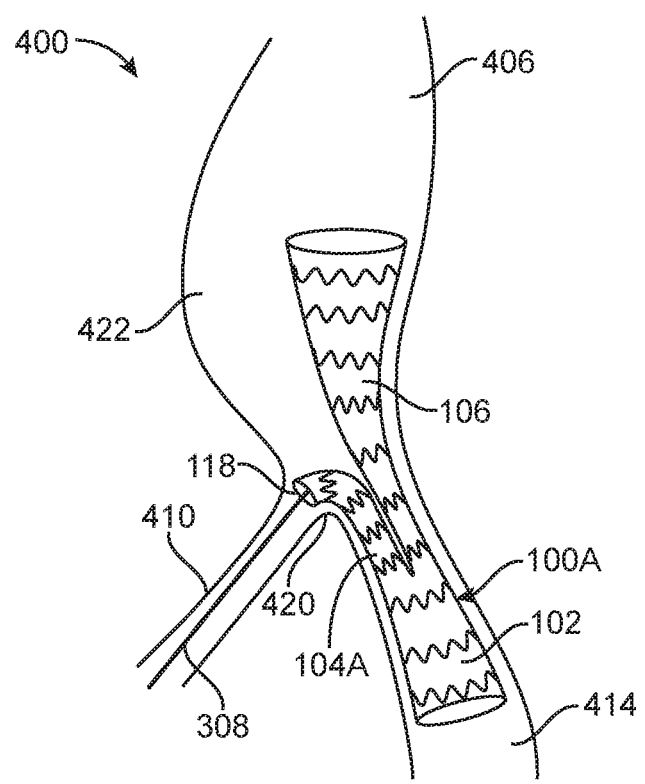
FIG. 7 is an enlarged view of the region V of the vessel assembly of FIG. 4 after deployment of the iliac branch device of FIG. 2 in accordance with one embodiment.

FIG. 7 is an enlarged view of the region V of vessel assembly 400 of FIG. 4 after deployment of iliac branch device 100A of FIG. 2 in accordance with one embodiment. The deployment of iliac branch device 100A of FIG. 7 is similar to the deployment of iliac branch device 100 of FIG. 5 and only the significant differences are discussed below.

In accordance with this embodiment, distal opening 118 of internal iliac branch 104A is located directly adjacent and proximal to the ostium of internal iliac artery 410. Due to the curvature of internal iliac branch 104A, distal opening 118 points towards the ostium of internal iliac artery 410. This simplifies cannulation of internal iliac artery 410 with guidewire 308 as the curvature of internal iliac branch 104A facilitates guiding of guidewire 308.

Figure 8:
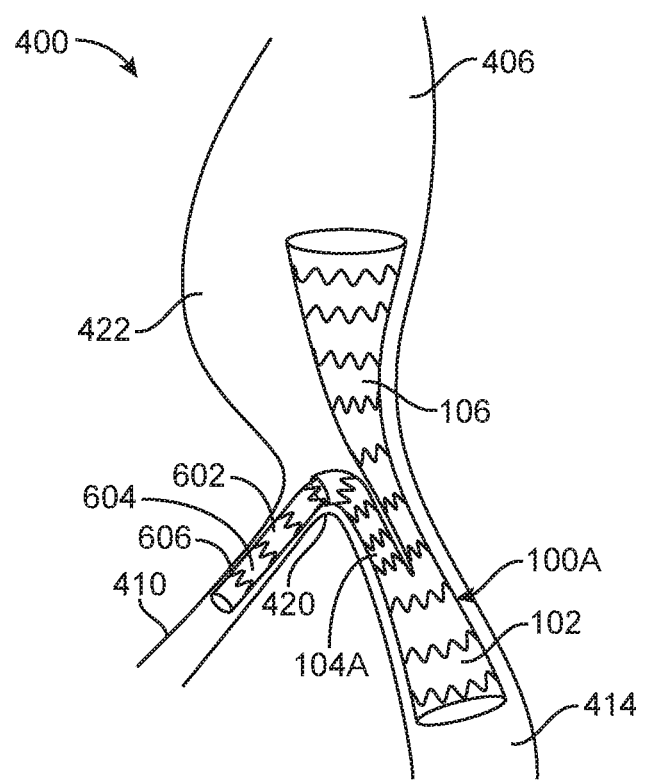
FIG. 8 is a partial cross-sectional view of the vessel assembly of FIG. 7 at a later stage during deployment of a bridging graft in accordance with one embodiment.

FIG. 8 is a partial cross-sectional view of vessel assembly 400 of FIG. 7 at a later stage during deployment of bridging graft 602 in accordance with one embodiment. Referring now to FIGS. 7 and 8 together, bridging graft 602 is deployed within internal iliac branch 104A and internal iliac artery 410 in a manner similar to that discussed above regarding deployment of bridging graft 602 into internal iliac branch 104 and internal iliac artery 410 of FIG. 6.

Figure 9:
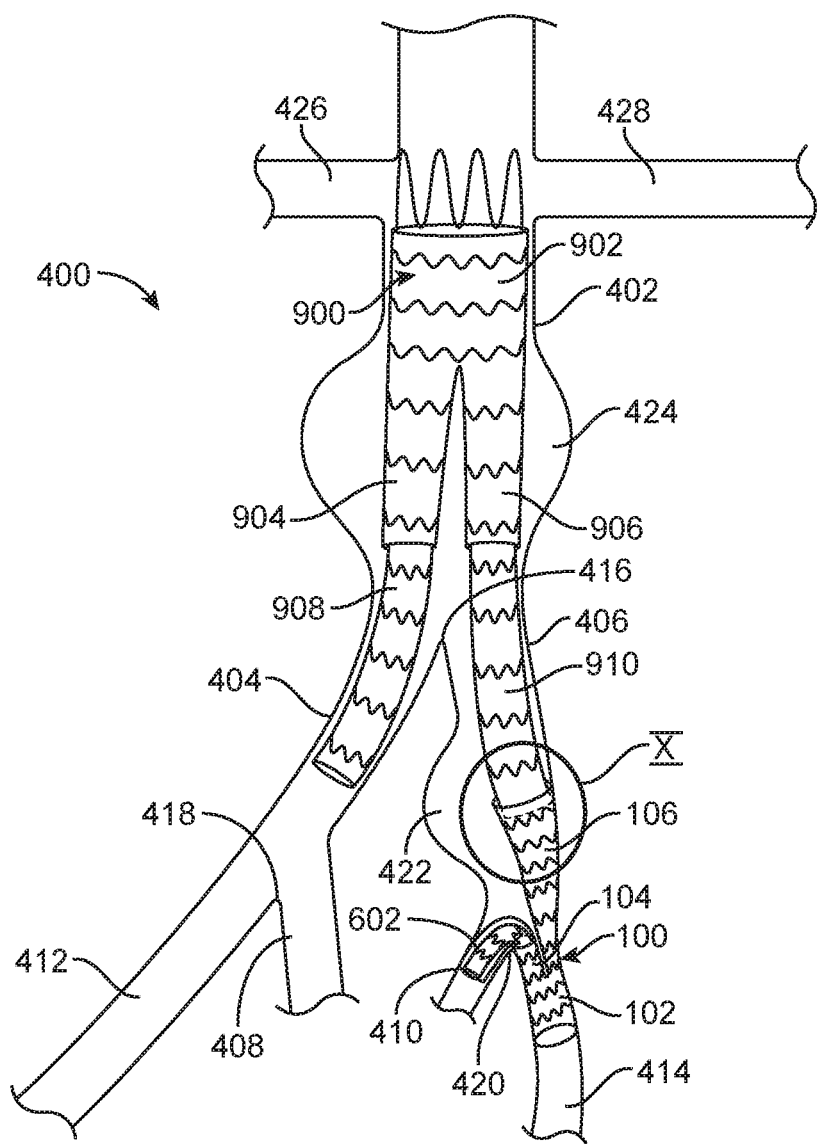
FIG. 9 is a partial cross-sectional view of the vessel assembly of FIG. 6 at a later stage after deployment of an aortic bifurcated stent graft in accordance with one embodiment.

FIG. 9 is a partial cross-sectional view of vessel assembly 400 of FIG. 6 at a later stage after deployment of an aortic bifurcated stent graft 900 in accordance with one embodiment. Referring now to FIGS. 4, 6, and 9 together, in accordance with this embodiment, aorta 402 includes an aortic aneurysm 424. In accordance with this embodiment, aortic bifurcated stent graft 900 excludes aortic aneurysm 424. However, in another embodiment, aorta 402 is healthy, i.e., does not include an aneurysm.

More particularly, aortic bifurcated stent graft 900 includes a main body 902, a first leg 904, and a second leg 906. Examples of aortic bifurcated stent graft 900 includes the Endurant® II AAA stent graft system manufactured by Medtronic or other AAA EVAR devices.

In one embodiment, aortic bifurcated stent graft 900 is deployed distal of renal arteries 426, 428 although the deployment location various in other embodiments depending upon the particular application of aortic bifurcated stent graft 900. A first bridging graft 908 is deployed within and bridges first leg 904 and common iliac artery 404. A second bridging graft 910 is deployed within and bridges second leg 906 and common iliac branch 106.

Figure 10A:
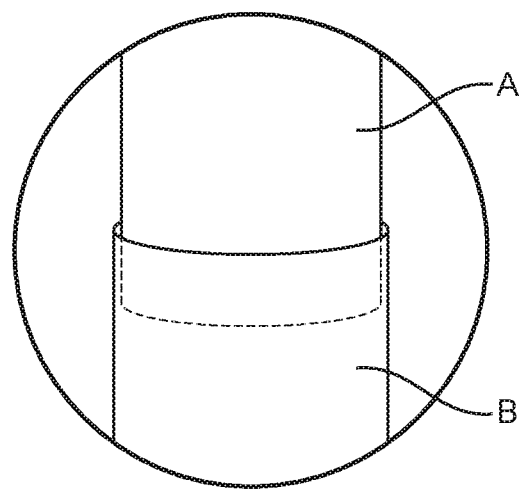
FIG. 10A is an enlarged view of the region X of the vessel assembly of FIG. 9 in accordance with one embodiment.

FIG. 10A is an enlarged view of the region X of vessel assembly 400 of FIG. 9 in accordance with one embodiment. FIG. 10A illustrates a first component A within a second component B.

Referring now to FIGS. 9 and 10A together, illustratively, aortic bifurcated stent graft 900 and iliac branch device 100 are initially deployed. After deployment of aortic bifurcated stent graft 900 and iliac branch device 100, bridging graft 910 is deployed within second leg 906 and common iliac branch 106. In accordance with this embodiment, first component A is representative of bridging graft 910 and second component B is representative of common iliac branch 106. As illustrated in FIG. 10A, bridging graft 910 (component A) is deployed within and overlaps common iliac branch 106 (component B) thus forming a seal between bridging graft 910 and common iliac branch 106.

Figure 10B:
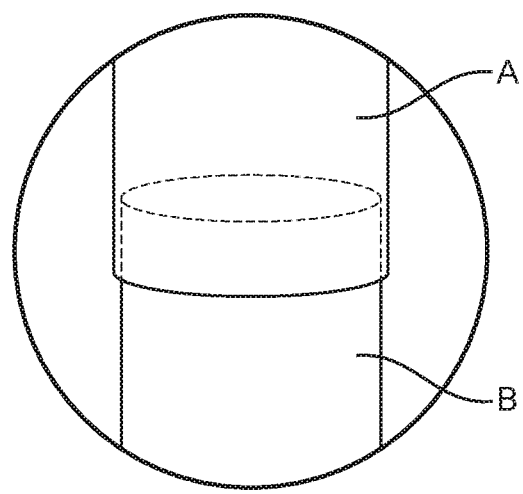
FIG. 10B is an enlarged view of the region X of the vessel assembly of FIG. 9 in accordance with another embodiment.

FIG. 10B is an enlarged view of the region X of vessel assembly 400 of FIG. 9 in accordance with another embodiment. FIG. 10B illustrates second component B within first component A.

Referring now to FIGS. 9 and 10B together, in accordance with this embodiment, aortic bifurcated stent graft 900 and bridging graft 910 are initially deployed. Illustratively, aortic bifurcated stent graft 900 and bridging graft 910 provide sufficient exclusion of aortic aneurysm 424.

However, after a period of time, aortic bifurcated stent graft 900 and bridging graft 910 do not provide sufficient exclusion. Illustratively, aortic aneurysm 424 grows and/or iliac aneurysm 422 is formed or grows. Accordingly, at a later point in time in a follow on procedure, iliac branch device 100 is deployed to provide sufficient exclusion of aneurysms 422 and/or 424.

More particularly, common iliac branch 106 is deployed within bridging graft 910. In accordance with this embodiment, first component A is representative of bridging graft 910 and second component B is representative of common iliac branch 106. As illustrated in FIG. 10B, common iliac branch 106 (component B) is deployed within and overlaps bridging graft 910 (component A) thus forming a seal between common iliac branch 106 and bridging stent graft 910.

In yet another embodiment, aortic bifurcated stent graft 900 and bridging stent graft 910 are initially deployed and iliac branch device 100 is then deployed in a single procedure.

Figure 11:
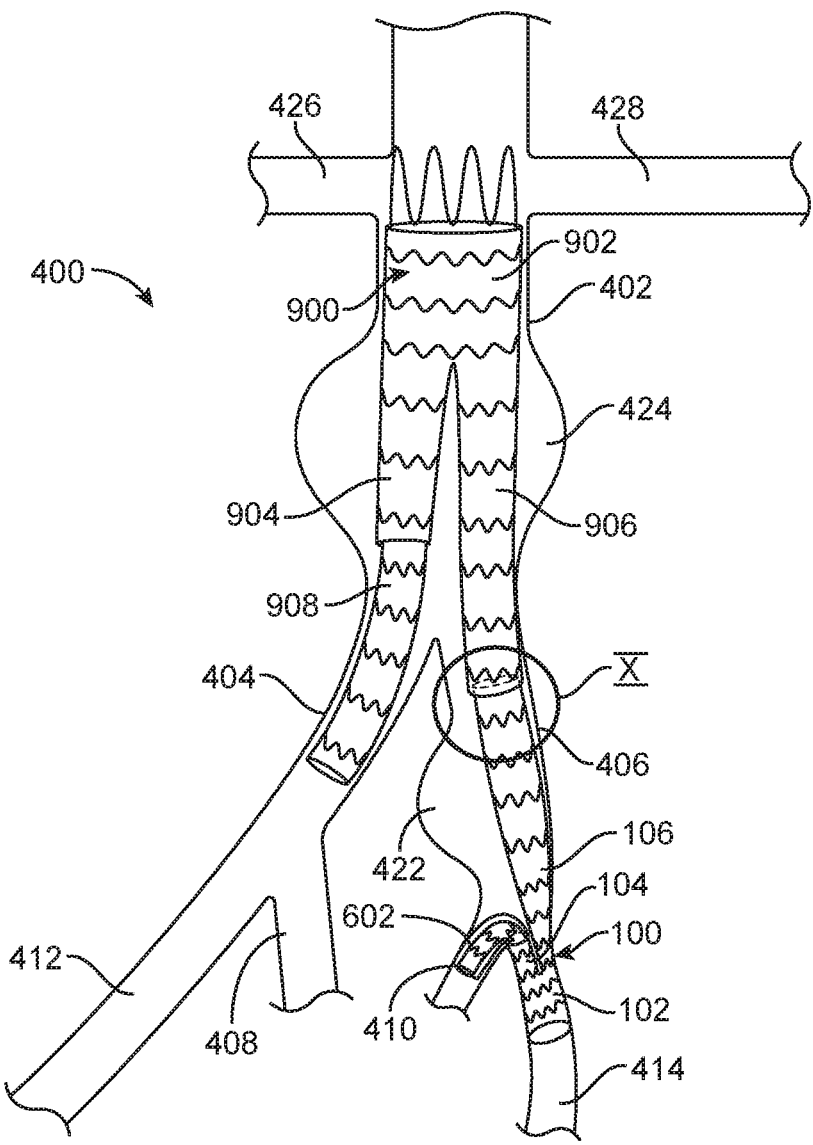
FIG. 11 is a partial cross-sectional view of the vessel assembly of FIG. 6 at a later stage after deployment of an aortic bifurcated stent graft in accordance with another embodiment.

FIG. 11 is a partial cross-sectional view of vessel assembly 400 of FIG. 6 at a later stage after deployment of aortic bifurcated stent graft 900 in accordance with another embodiment. Vessel assembly 400 as illustrated in FIG. 11 is similar to vessel assembly 400 as illustrated in FIG. 9 except bridging graft 910 of FIG. 9 is not used in accordance with the embodiment of FIG. 11.

Referring now to FIGS. 4, 6, and 11 together, in accordance with this embodiment, common iliac branch 106 is joined directly with second leg 906 of aortic bifurcated stent graft 900. Illustratively, second leg 906 and/or common iliac branch 106 are extended to overlap one another.

FIG. 10B is an enlarged view of the region X of vessel assembly 400 of FIG. 11 in accordance with this embodiment. Referring now to FIGS. 10B and 11 together, in accordance with this embodiment, aortic bifurcated stent graft 900 is initially deployed. Illustratively, aortic bifurcated stent graft 900 provides sufficient exclusion of aortic aneurysm 424.

However, after a period of time, aortic bifurcated stent graft 900 does not provide sufficient exclusion. Illustratively, aortic aneurysm 424 grows and/or iliac aneurysm 422 is formed or grows. Accordingly, iliac branch device 100 is deployed to provide sufficient exclusion of aneurysms 422 and/or 424.

More particularly, common iliac branch 106 is deployed within second leg 906. In accordance with this embodiment, first component A is representative of second leg 906 and second component B is representative of common iliac branch 106. As illustrated in FIG. 10B, common iliac branch 106 (component B) is deployed within and overlaps second leg 906 (component A) thus forming a seal between common iliac branch 106 and second leg 906.

In yet another embodiment, aortic bifurcated stent graft 900 is initially deployed and iliac branch device 100 is then deployed in a single procedure.

Figure 12:
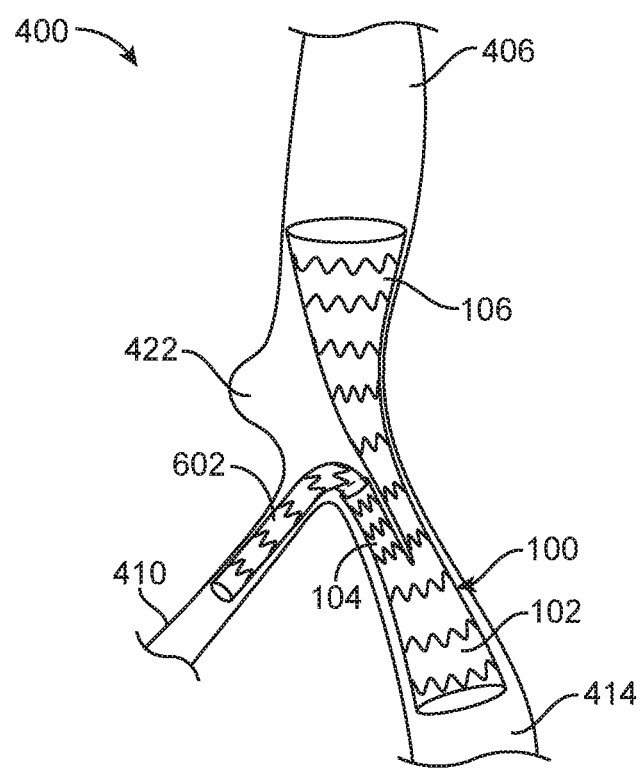
FIG. 12 is an enlarged view of the region V of the vessel assembly of FIG. 4 in accordance with one embodiment.

FIG. 12 is an enlarged view of the region V of vessel assembly 400 of FIG. 4 in accordance with one embodiment. Referring to FIGS. 4 and 12 together, in accordance with this embodiment, vessel assembly 400 includes only an isolated iliac aneurysm 422. In accordance with this embodiment, iliac branch device 100 alone provides sufficient exclusion of iliac aneurysm 422. Illustratively, common iliac branch 106 forms a proximal seal with common iliac artery 406. External iliac body 102 forms a distal seal with external iliac artery 414. Internal iliac branch 104 and bridging graft 602 form the distal seal with internal iliac artery 410. In this manner, isolated iliac aneurysm 422 is excluded by iliac branch device 100 alone.

In one embodiment, after a period of time, iliac branch device 100 does not provide sufficient exclusion. Illustratively, aortic aneurysm 424 is formed and/or iliac aneurysm 422 grows. Accordingly, aortic bifurcated stent graft 900 is deployed to provide sufficient exclusion of aneurysms 422 and/or 424.

More particularly, referring to FIGS. 10A, 11-12, second leg 906 of aortic bifurcated stent graft 900 is deployed with common iliac branch 106. In accordance with this embodiment, first component A is representative of second leg 906 and second component B is representative of common iliac branch 106. As illustrated in FIG. 10A, second leg 906 is deployed within and overlaps common iliac branch 106 thus forming a seal between common iliac branch 106 and second leg 906.

In yet another embodiment, iliac branch device 100 is initially deployed and aortic bifurcated stent graft 900 is then deployed in a single procedure.

Although FIGS. 9, 10A, 10B, 11 and 12 are discussed above as including iliac branch device 100 of FIG. 1, in other embodiments, iliac branch device 100A as illustrated in FIG. 2 is used in place of iliac branch device 100. Accordingly, the discussion regarding iliac branch device 100 in FIGS. 9, 10A, 10B, 11-12 is equally applicable to iliac branch device 100A.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An assembly comprising:
a delivery system comprising a handle; and
an iliac branch device loaded within the delivery system, the iliac branch device comprising:
an external iliac body comprising a distal opening;
a common iliac branch comprising a proximal opening, a diameter of the proximal opening being greater than a diameter of the distal opening; and
an internal iliac branch configured to perfuse an internal iliac artery,
wherein the entire external iliac body is proximal to both the common iliac branch and the internal iliac branch relative to the handle when the iliac branch device is loaded in a delivery state within the delivery system,
wherein the internal iliac branch and the common iliac branch are side by side when the iliac branch device is loaded in the delivery state.

2. The assembly of claim 1 wherein the external iliac body is distal to the common iliac branch.

3. The assembly of claim 1 wherein the external iliac body is bifurcated into the common iliac branch and the internal iliac branch at a transition region.

4. The assembly of claim 3 wherein a proximal end of the external iliac body is coupled to a proximal end of the internal iliac branch and a distal end of the common iliac branch.

5. The assembly of claim 4 wherein the distal opening of the external iliac body is at a distal end of the external iliac body and the proximal opening of the common iliac branch is at a proximal end of the common iliac branch.

6. The assembly of claim 5 wherein the internal iliac branch comprises a distal opening at a distal end of the internal iliac branch.

7. The assembly of claim 6, wherein the external iliac body comprises a lumen extending between the distal opening of the external iliac body and transition region,
wherein the internal iliac branch comprises a lumen extending between the distal opening of the internal iliac branch and the transition region, and
wherein the common iliac branch comprises a lumen extending between the proximal opening of the common iliac branch and the transition region.

8. The assembly of claim 1 wherein a curving member is configured to cause the internal iliac branch to curve away from the common iliac branch.

9. The assembly of claim 8 wherein the curving member comprises a wire secured to the internal iliac branch.

10. The assembly of claim 9 wherein the wire is located on an inner curve of the internal iliac branch.

11. The assembly of claim 9 wherein the curving member comprises multiple wires comprising the wire.

12. The assembly of claim 8 wherein the curving member comprises stitching.

13. The assembly of claim 8 wherein the curving member is configured to cause the internal iliac branch to have a hook shape.

14. An assembly comprising:
a delivery system comprising:
a handle;
an inner member; and
a second inner member; and
an iliac branch device loaded within the delivery system, the iliac branch device comprising:
an external iliac body configured to be located within an external iliac artery;
a common iliac branch configured to be located with a common iliac artery; and
an internal iliac branch configured to perfuse an internal iliac artery,
wherein the entire external iliac body is proximal to both the common iliac branch and the internal iliac branch relative to the handle when the iliac branch device is loaded in a delivery state within the delivery system,
wherein the inner member is located within the external iliac body and the common iliac branch and exits a proximal opening of the common iliac branch; and
wherein second inner member is located within the external iliac body and the internal iliac branch and exits a distal opening of the internal iliac branch.

15. The assembly of claim 14 further comprising a sheath constraining the iliac branch device.

16. The assembly of claim 14 further comprising a first guidewire within a lumen of the inner member.

17. The assembly of claim 16 further comprising:
a second guidewire within a lumen of the second inner member.

18. The assembly of claim 14, wherein the external iliac body comprises a distal opening,
wherein a diameter of the proximal opening of the common iliac branch is greater than a diameter of the distal opening of the external iliac body.

19. A method comprising:
loading an iliac branch device within a delivery system comprising a handle, the iliac branch device comprising:
an external iliac body;
a common iliac branch; and
an internal iliac branch,
wherein the entire external iliac body is proximal to both the common iliac branch and the internal iliac branch relative to the handle when the iliac branch device is loaded in a delivery state within the delivery system, and
wherein the internal iliac branch and the common iliac branch are side by side when the iliac branch device is loaded in the delivery state.

20. The method of claim 19 further comprising:
introducing the delivery system through an ipsilateral external iliac artery access point;
advancing the delivery system to a deployment location; and
deploying the iliac branch device at the deployment location, wherein the external iliac body is located within an external iliac artery and the common iliac branch is located within a common iliac artery.

21. The method of claim 20 further comprising deploying a bridging graft within the internal iliac branch and an internal iliac artery.

22. The method of claim 20 further comprising deploying an aortic bifurcated stent graft in an aorta, wherein the common iliac branch is directly coupled to a leg of the aortic bifurcated stent graft.

23. The method of claim 20 further comprising deploying an aortic bifurcated stent graft in an aorta, wherein the common iliac branch is coupled to a leg of the aortic bifurcated stent graft by a bridging graft.

* * * * *